United States Patent [19]

Bates et al.

[11] 3,947,568

[45] Mar. 30, 1976

[54] EFFERVESCENT COSMETIC COMPOSITIONS

[75] Inventors: Barstow Bates, Old Greenwich, Conn.; Norman H. Ishler, Valley Cottage, N.Y.

[73] Assignee: Phoenix Research Inc., Las Vegas, Nev.

[22] Filed: Jan. 4, 1974

[21] Appl. No.: 430,617

Related U.S. Application Data

[63] Continuation of Ser. No. 60,762, Aug. 3, 1970, abandoned, which is a continuation-in-part of Ser. No. 689,351, Dec. 11, 1967, abandoned.

[52] U.S. Cl. .................. 424/47; 424/45; 424/73
[51] Int. Cl.² .................. A61K 9/00; A61K 9/04
[58] Field of Search.......................... 424/45, 47

[56] References Cited
UNITED STATES PATENTS

| | | | |
|---|---|---|---|
| 2,655,486 | 10/1953 | Spitzer et al............................ | 252/90 |
| 2,995,521 | 8/1961 | Bluard................................... | 252/90 |
| 3,092,555 | 6/1963 | Horn................................... | 424/45 X |
| 3,131,153 | 4/1965 | Klausner............................. | 252/305 |
| 3,144,386 | 8/1964 | Brightenback........................ | 424/45 |
| 3,282,781 | 11/1966 | Macek et al.......................... | 424/45 |
| 3,304,230 | 2/1967 | Abramson............................. | 424/45 |

OTHER PUBLICATIONS

Chemical Abstracts –6th C8DLL Index, Vol. 51–55 (1957–1961) 4972s.

*Primary Examiner*—Leonard Schenkman
*Attorney, Agent, or Firm*—Flynn & Frishauf

[57] ABSTRACT

Cosmetic compositions exhibiting effervescence comprise a cosmetic agent and a liquefied gas distributed therethrough. The liquefied gas is present in the compositions at pressure and temperature conditions at which it would normally exist only in the gaseous state. As the liquefied gas separates from the compositions, effervescence occurs.

9 Claims, No Drawings

EFFERVESCENT COSMETIC COMPOSITIONS

RELATED APPLICATIONS

This is a continuation of application Ser. No. 60,762 filed Aug. 3, 1970, which is a continuation-in-part of application Ser. No. 689,351 filed Dec. 11, 1967, both now abandoned.

This application is related to each of the following copending applications for Letters Patent filed Dec. 11, 1967, namely: Ser. No. 689,266 which is directed to effervescent products, particularly food compositions; Ser. No. 689,292 which is directed to effervescent cleansers; and Ser. No. 689,278, which is directed to effervescent medicaments.

FIELD OF INVENTION

This application has to do with effervescent cosmetic compositions and to a process for preparing the same.

DEFINITIONS

As used herein, the term "effervescence" is in the context of a new effervescent principle. This effervescence is characterized by strong initial bubbling accompanied by pronounced auditory effects, namely, "pinging" and "popping" sounds, when an effervescent medium is discharged into an aqueous or alcoholic liquid. The bubbling and auditory effects subside in intensity gradually but continue for hours at room temperature.

Any aqueous liquid containing the effervescent medium will show unique behavior in the mouth. The liquid will create the sensation of swirling about in the mouth and as the effervescent material strikes the buccal surfaces it imparts a tingling feeling as well as occasional internal clicking sounds in the head.

When the effervescent medium is incorporated into a more viscous liquid such as a hand lotion, pomade or skin cream the auditory and bubbling effects are much dimished but a tingling sensation imparted to the external body surface at the moment of contact is pronounced.

As discussed in detail below, this type of effervescence is in contrast with conventional effervescence wherein bubbles of gas escape from a liquid otherwise than by boiling.

BACKGROUND OF THE INVENTION

Effervescence is a widely used, desirable and useful property of many commercial products. Notable among these are carbonated soft drinks, stomach distress medications in the form of pills or powders which are added to water immediately before consumption, soft drink tablets or powders which effervesce upon dissolving in water, quick dissolving pills, tablets, denture cleansers, etc. Virtually all effervescing products intended for consumer use are based on the evolution of the gas, carbon dioxide. Others are based on the evolution of oxygen as from perborates, peroxides and the like.

In liquid products such as carbonated beverages, the carbon dioxide is dissolved in the water of the beverage under pressure prior to bottling, canning, or mixing with flavored syrup as in a conventional soda fountain. Sufficient pressure is maintained on the carbon dioxide solution to retain that gas in solution until the product is ready to be used. When the bottle or other container is opened or the liquid is discharged from a pressurized, soda-water siphon bottle or from a pressurized storage tank in a soda fountain, the aqueous solution of carbon dioxide immediately becomes supersaturated at atmospheric pressure and some of the dissolved carbon dioxide begins to come out of solution in the form of tiny bubbles of gas which are released continuously and for an extended period of time.

Most effervescent solid products such as powders and tablets, are prepared by incorporating therein suitable quantities of reactive ingredients, namely, an acidic material and a carbonate such as sodium bicarbonate. As long as the resulting mixture (e.g., tablet) remains dry, these reactive ingredients do not produce any significant amount of carbon dioxide. However, when the products are added to water, both reactive ingredients dissolve and are thus enabled to react with each other creating a desired amount of evolution of carbon dioxide gas, one of the end products of the reaction. Generally, this reaction proceeds rapidly so that the acidic and alkaline ingredients are neutralized and the effervescence essentially stops, although there may be a slow release of carbon dioxide which has dissolved to a minor extent in the water during the vigorous evolution phase. Normally, however, the effervescence does not continue nearly as long as the effervescence created by dissolving carbon dioxide in water under pressure. This is because the carbon dioxide created by the reaction of acidic constituents and sodium bicarbonate does not dissolve to any great extent in the water, since the entire system is usually at atmospheric pressure during the time the gas is being generated and is bubbling through the aqueous medium. Hence, the carbon dioxide merely passes through the liquid and effervescence ceases almost completely as soon as the generation of gas by chemical reaction is complete.

It can be seen from the foregoing that the application of effervescent properties to various types of products is generally limited to situations where dissolved gases may be allowed to be released from the solutions in which they have previously been dissolved or where gases may be created by chemical reaction during or immediately preceeding the time of use of these products.

The present invention is predicated upon a different principle for the purpose of creating a vigorous, relatively long-lasting, auditory effervescence in a wide variety of types of products. It has been found that certain compounds, liquefied gases, which are immiscible with a matrix can be retained essentially completely in the liquid phase with only a slow boiling occurring at temperatures which are significantly higher than the boiling point of these liquids at the prevailing environmental pressure.

Liquefied gases, such as fluorinated hydrocarbons are commonly used as propellants for various types of aerosol products such as paints, insecticides, waxes, whipped toppings for foods, and many other types of end products, which are retained in aerosol containers. When the pressure is released by means of a valve on the aerosol container, the contents of the pressurized container are discharged and any liquefied gas propellant which is discharged from the container vaporizes essentially instantaneously as the contents of the container enter the much lower pressure zone (atmospheric pressure) outside of the container. Frequently, liquefied gas propellants are combined with dissolved gas propellants and these dissolved propellants also tend to vaporize instantaneously upon release fom the pressurized container and combinations of the formerly liquefied gas and the dissolved gas create bubbles or foam in the product as discharged. This type of product is exemplified by shaving creams and whipped toppings. Little or no liquefied gas is retained in the dispensed product, thus the product is characterized by little or no effervescence.

There are many products described in patents and in technical literature which describe the use of liquefied gases as propellants for products contained in aerosol containers. Frequently, these liquefied gases not only propel the product from the container but some of the liquefied gas emerges with the product from the container and serves the further purpose of creating a foam by vaporizing essentially instantaneously as the pressure is released upon leaving the container. Sometimes the liquefied gas is used as a dispersant for other liquids after the product leaves the aerosol container as in the case with insecticide sprays, deodorant sprays, or the like. In this instance also, the liquefied gas performs its function by vaporizing essentially instantaneously as the product leaves the aerosol container and the internal pressure is released. In still another conventional use of liquefied gases, substances such as medicaments, antiperspirants, waxes, etc. may be dissolved in the liquefied gas within the aerosol container. When these products are discharged from the container, the propellant is intended to vaporize essentially instantaneously, depositing a film or a dusting of the previously dissolved active ingredient upon the surface to which the stream or spray is directed. Hair sprays or lacquers are also typical examples of this type of use of a liquified propellant. Still another common use of liquefied gas propellants is to serve as a means of discharging dry, insoluble materials such as talc or lubricating powders like graphite from an aerosol container. In these instances the dry material is shaken with the liquid propellant in the container immediately before discharge, the dry ingredient thereupon being dispersed and leaving the container in the stream of liquefied gas as a dispersing solid. Upon emerging from the container the liquefied gas vaporizes essentially instantaneously, depositing a thin film or dusting of the dry material upon any surface toward which the stream or spray is directed.

Accordingly, there has been no previous description of the use of a liquefied gas, not only to propel the contents of an aerosol container out of that container but also wherein some of the liquefied gas is dispersed throughout the aqueous or alcoholic matrix of the contents of the can and serves as a source of vigorous bubbling and effervescence in the products which are produced by so discharging some of the can contents into a vessel, on a surface, or into other liquids in a vessel. No previously described products, at the time of use, comprise liquid matrices containing dispersed therethrough or at the bottom thereof substantial quantities of liquefied gases which exist as liquids boiling slowly and continuously for long periods of time (one-half hour up to 24 hours or longer) at atmospheric pressure and at temperatures which may be as much as 100°F. above the expected boiling point of said liquefied gases.

SUMMARY OF THE INVENTION

In contrast to the foregoing known products employing liquefied gases, a new class of products containing liquefied gases has been discovered.

In accordance with the present invention, there are provided effervescing cosmetic compositions formed by:

A. maintaining in an aerosol container (a) a liquefied gas and (b) an aqueous or alcoholic phase containing a cosmetic, said phase being substantially nonsoluble with (a) and being dispersible with (a) with agitation thereof, (a) having a density greater than (b) and the quantity of (a) being substantially in excess of the quantity sufficient to propel (b) from said container, B. agitating the aerosol container whereupon (a) is dispersed in (b), and C. while (a) and (b) are interdispersed, discharging contents of the container as a liquid stream into a vessel, some of the dispersed phase (a) remaining dispersed after the contents leave the container and vaporizing steadily, creating continuing effervescence.

There is also provided a method for producing an effervescent cosmetic composition comprising:

A. charging to an aerosol container (a) a liquefied gas and (b) an aqueous or alcoholic phase containing a cosmetic, said phase being substantially non-soluble with (a) and being dispersible with (a) with agitation thereof, (a) having a density greater than (b) and the quantity of (a) being substantially in excess of the quantity sufficient to propel (b) from said container, B. agitating the aerosol container whereupon (a) is dispersed in (b), and C. while (a) and (b) are interdispersed, discharging contents of the container as a liquid stream into a vessel, some of the dispersed phase (a) remaining dispersed after the contents leave the container and vaporizing steadily, creating continuing effervescence.

SPECIFIC EMBODIMENTS OF THE INVENTION

The compositions of this invention are characterized as liquids which bubble vigorously in a manner similar to, but much more vigorously if desired, than ordinary carbonated liquids. These compositions have essentially the same visual appearance as a conventional carbonated composition except that the bubbling may be much more vigorous. These compositions differ from ordinary carbonated compositions in that, typically, the bubbling is much more audible than a carbonated composition, producing a distinct hissing or a "pinging" sound as bubbles are formed, rise through the liquids, and break at the surface. These compositions also differ from ordinary carbonated compositions in that they comprise a three phase system: a liquid, aqueous matrix comprising 99% or more of the product; an immiscible liquid phase which is a liquefied gas at a temperature between about 5°F. and about 100°F. above its boiling point at atmospheric pressure; and a gas in the form of bubbles rising through the aqueous phase as this gas is vaporized from the liquefied gas phase.

In the practice of this invention, the liquefied gas is selected to have a liquid density greater than the density of the aqueous phase so that the liquefied gas can remain suspended as small droplets in, or settle to the bottom of the aqueous phase. A liquefied gas which is lower in density than the aqueous phase will tend to rise to the surface of said aqueous phase where it will boil or vaporize without creating any visible or audible bubbles throughout the aqueous phase. The exact density of the liquefied gas is not important, so long as it is greater than the density of the aqueous phase.

The presence of a liquefied gas phase in the new compositions is generally not noticeable to the user, since either: (a) the liquefied gas is dispersed throughout the aqueous phase in tiny droplets which cannot be distinguished from the gas bubbles rising to the surfaces of the aqueous phase or (b) the liquefied gas settles to the bottom of the aqueous matrix as a very thin film which can be observed in most instances only upon very careful observation. In the practice of this invention either the dispersed droplets or the thin film of liquefied gas continue to vaporize slowly, thereby generating bubbles of gas either throughout the body of the aqueous matrix or at the bottom of the matrix, from which point the bubbles rise throughout the entire volume of the product with a visual appearance similar to that of carbonated compositions.

Another unusual and unexpected characteristic of this invention relates to the slow and continued boiling of these super-heated, liquefied gases. Those skilled in the applications of the science of chemistry or physical chemistry are very familiar with super-heated liquids. In particular, numerous organic liquids can be heated to several degrees above their boiling point, particularly in the absence of vigorous agitation or activating surfaces which would tend to provide nucleation centers for the formation of gaseous bubbles. Such super-heated organic liquids may remain quiescent without active boiling or ebullition. However, once initiated by scratching the interior surface of the vessel in which the liquid is contained, or by introducing some solid such as sand or glass beads or activated charcoal, etc. which provides new surfaces whereupon gas bubbles can begin to form, extremely vigorous boiling will immediately occur until sufficient liquid has vaporized to reduce the temperature of the remaining body of liquid to its normal boiling point or slightly below, whereupon boiling ceases. The boiling of the super-heated liquefied gases in the products of the present invention differs markedly and unexpectedly from the above-described behavior of many organic liquids in that the super-heated liquefied gases of the present invention boil steadily, slowly and continuously for periods of time ranging from one-half hour to several hours without the violent ebullition mentioned above.

Liquefied gases can be restrained from immediate or essentially instantaneous vaporization when the product leaves the pressurized container so that significant quantities of liquefied gas, usually in the form of small droplets, remain in the liquid phase in the product after it has been discharged from the aerosol container and is essentially at atmospheric pressure conditions. These liquefied gas substances can be considered to be in a metastable state, since they are still liquid at temperatures well above their boiling points at the prevailing (essentially atmospheric) pressure outside of the pressurized aerosol container. They can also be considered to be superheated for the same reasons. Typically, these superheated liquids will boil at either a rapid or slower rate, depending on conditions, thereby tending to go from the metastable (liquid) phase to the stable (gas) phase.

Cosmetics of all varieties can be employed, including: facial preparations such as complexion lotions, hand lotions and creams, bath oils, foot bath preparations, colognes, shaving creams, after-shave lotions, deodorants, depilatories and hair creams. All of such compositions will contain one or more recognized cosmetic agents.

A variety of liquefied gases are suitable for the cosmetic compositions of this invention. Generally, the boiling points thereof will range from about −50°F. to about 80°F. Preferably, materials cleared for food and drug use are employed. Typical of such materials are octafluorocyclobutane (duPont's Freon C-318); boiling point, 21.5°F.; vapor pressure, 25.4 psig. at 70°F.) and monochloropentafluoroethane (duPont's Freon 115; boiling point, −37.7°F.; vapor pressure, 103 psig. at 70°F.), and mixtures thereof. With products not requiring such clearance, other typical liquefied gases can be employed. These include the aforementioned halogenated materials and other related materials:

chlorodifluoromethane (Freon -22)
dichlorodifluoromethane (Freon -12)
1,2-dichloro-1,1,2,2-tetrafluoroethane (Freon -114)
dichloromonofluoromethane (Freon -21)
trichloromonofluoromethane (Freon -11).

Liquefied hydrocarbon gases which can be used include propane, butane, isobutane, cyclobutane and pentane. Mixtures of all such liquefied gases are contemplated.

Individual liquefied gas compounds or mixtures thereof, however, must be selected to have densities greater than the density of the effervescent liquid product in which they are to be used. All of the fluorinated hydrocarbons mentioned, typically have liquid densities considerably greater than one and hence greater than any of the aqueous matrices in which they might be used. Liquefied hydrocarbons, however, such as those mentioned above, typically have densities much lower than one and hence if used singly, would tend to float on top of the aqueous medium, boiling from the surface, and therefore not producing bubbles throughout the liquid matrix. Therefore, these liquefied hydrocarbon gases can be used for most applications only in admixture with more dense liquefied gases such that the mixture has a density high enough (e.g. greater than 1) to permit the liquefied mixture to settle below the surface of the liquid matrix.

It is also important that any liquefied gas used to create effervescence in a liquid medium should be substantially immiscible with that liquid medium.

The products of this invention can contain dissolved gases together with the liquefied gases defined above. Carbon dioxide, nitrous oxide, and air are illustrative of such dissolved gases.

Since relatively small amounts of liquefied gases will produce relatively large amounts of vapors, that is, have high expansion ratios upon evaporation, only relatively small quantities of liquefied gases need be employed in a matrix in order to provide considerable effervescence. By way of illustration, the expansion ratio of octafluorocyclobutane on evaporation at 70° F. is 175:1.

As a further illustration, less than 1 ml. of a liquefied gas such s octafluorocyclobutane or a mixture of that gas with up to 27.5% of monochloropentafluoroethane is sufficient, when dispersed throughout or when settled to the bottom of an 8 oz. glass of beverage to produce vigorous effervescence for continued period of times (much more vigorous than conventional carbonated beverages, but otherwise similar to the effervescence of a carbonated beverage). 1 ml. of liquefied gas, therefore, being capable of generating 175 ml. of gas in the vapor phase, is roughly equivalent to providing one volume of gas for each volume of the liquid matrix (the beverage) in which it is entrapped.

The extent of the effervescence and the length of time during which effervescence will continue will vary considerably, being influenced by such factors as the character of the matrix, temperature, pressure and other factors.

Thus, for example, in aerosol use, the liquefied gas is present in an aerosol container substantially in excess of the quantity necessary to serve as a propellant to expel the contents of the container. The quantity of liquefied gas will vary widely with the pressure of the liquefied gas at the time of discharge of the contents from the container. For example, the volume of a so called 8 oz. aerosol container is 300 ml. In the normal use of liquefied gas as a propellant only (not for effervescence), it is necessary to supply enough liquefied gas to vaporize in the container as the liquid matrix is discharged so that, when all of the non-propellant contents of the can are discharged, the can will be full of vaporized propellant at a pressure equal to the vapor pressure of that propellant at the temperature at which the non-propellant contents are discharged. Examples of the amount of liquefied gas required to vaporize and completely fill a 300 ml. container with vaporized propellant at its vapor pressure at 77°F. are as follows:

| Liquefied Gas Propellant | Grams required | Ml. required |
|---|---|---|
| Octafluorocyclobutane (C-318) | 7.92 | 5.35 |
| 1,2-Dichloro-1,1,2,2-Tetrafluoroethane (Freon 114) | 4.6 | 3.16 |
| 27.5% Monochloropentafluoroethane (Freon 115) (72.5%) Octafluorocyclobutane (Freon C-318) | 12.34 | 8.34 |

The above figures are the minimum required to serve only as a propellant if none of the liquefied gas is to be allowed to escape in liquid form as the remainder of the contents of the container are discharged. In order to provide effervescence in the product after it is discharged from the aerosol container, it is necessary to supply sufficient excess of liquefied gas in excess of the amount required to propel the contents so that some of the liquefied gas will be entrained in the stream leaving the aerosol container and will remain in the liquid matrix after some quantity of contents has been discharged to bubble and boil and create effervescence in the context of this invention. Generally, an excess of at least about 5 percent by weight of the container contents is employed.

The products of this invention can be packaged in a wide variety of containers. As indicated, conventional aerosol containers can be used; so also, conventional cans, bottles, sealed tubular, paperboard units and others.

A number of factors influence the nature of the effervescence which characterizes the new products. However, in no sense is the invention limited to any theory of behavior. Temperature is one such factor. For example, a refrigerated aerosol container (at 40°F.) in which a cosmetic composition and a liquefied gas are confined, is discharged into a container of water, with the result that an exceptionally vigorous gas evolution occurs with very little foam formation. This vigorous and "noisy" gas evolution continues for several minutes; then the gas evolution slows to a minimum level sooner than is the case when a corresponding container is maintained at room temperature (65°–75°F.) and the contents thereof are discharged into water. When a similar aerosol container at room temperature (e.g. about 70°F.) is discharged into an aerosol solution, the velocity and force of the emerging stream is greater than when the discharge occurs from a container at refrigerator temperature. This is because the vapor pressure of the liquefied propellant inside the aerosol container is greater at room temperature than at refrigerator temperature, thus forcing the discharge stream out of the spout of the aerosol container at a higher velocity. Also, as the stream leaves the spout of the aerosol container and before it impinges upon the surface of the liquid into which it is being discharged, there is more tendency for some of the entrapped liquefied propellant to vaporize than is the case when a refrigerated container is used. Because of the force of the higher velocity stream from the room temperature container, the liquefied gas droplets tend to be broken up into smaller droplets in the aqueous liquid in the receiving container and smaller bubbles of vaporized gas (from the liquefied gas) are generated than would be the case if the aerosol container had been refrigerated at the time of discharge. This vigorous generation of hundreds or thousands of extremely small gas bubbles gives rie to a distinct hissing sound as opposed to the pinging sound created by larger bubbles forming and the multiplicity of tiny gas bubbles may temporarily create a cloudiness in the aqueous solution into which the product was discharged. However, within a minute or two the tiny droplets of liquefied gas coalesce into larger droplets and gradually tend to settle toward the bottom of the receiving container, after which the effervescent characteristics of the product in the receiving container are essentially like those created by discharging the same matrix (with its liquefied gas) from an aerosol container at refrigerator temperature.

Interfacial tension between a liquefied gas and other components of a product is considered to exert an influence upon the nature of the effervescence produced. Such interfacial tension should be sufficient to substantially retard the separation of the vapors of the liquefied gas from still liquefied gas and the matrix, and thereby retard the escape of the liquefied gas as a vapor from the product. The escape of vapors of the liquefied gas is preferably retarded in order that a substantial portion thereof is retained in the product for at least about one minute and preferably for longer time intervals.

Typically, the products of this invention will bubble vigorously for at least five minutes and then at a gradually reduced rate of effervescence. Within one-half hour to about 1 hour, the rate of bubbling will decrease to an almost imperceptible amount if the container into which the effervescent product has been discharged is not agitated. Upon jarring the container or agitating it by swishing or stirring, noticeable and distinct bubbling will reoccur and will usually continue for several minutes after such agitation has ceased. Some of the liquefied gas, if not disturbed, will remain in the liquid phase at 40° to 100°F. above its boiling point in an aqueous medium for suprisingly long periods of time. It has frequently been observed that most of the effervescent products of this invention, if not agitated, will bubble vigorously for one-half hour to 1 hour after first being discharged and then may rest with only an occasional bubble of gas being generated for periods of up to 48 hours. Thereafter, upon agitation, bubbling will begin again although at a rate considerably less than the initial vigorous effervescence characteristic of these products.

The pH of an aqueous phase in contact with the liquefied gas in an aerosol container seems to have negligible effect upon the effervescence characteristic of the products of this invention after they have been discharged from the aerosol container into a suitable vessel. Excellent bubbling action has been obtained when an aqueous matrix in aerosol containers was adjusted in a range of pH's from 1 to 12. This is not unexpected since the factors which control effervescence appear to be physical or physical chemical in nature, rather than chemical, due to the chemical inertness of the liquefied gases most commonly used (fluorinated hydrocarbons).

Data indicates that the mutual solubility of the aqueous phase and the liquefied gas phase in an aerosol container influence the rate of effervescent bubbling when aerosol can contents are discharged into a vessel or into another liquid. For example, a liquefied gas comprising a mixture of 27% monochloropentafluoroethane and 73% octafluorocyclobutane is less effective as a source of effervescence when combined in an aerosol container with an aqueous alcohol solution such as a solution of 50% alcohol in water, than is a liquefied gas comprising 100% octafluorocyclobutane. This is believed to be due to the fact that monochloropentafluoroethane is completely miscible in all proportions with alcohol, whereas octafluorocyclobutane will dissolve only a maximum of 18% of ethyl alcohol. It is desirable, therefore, in the practice of this invention, to avoid or minimize the use of liquefied gas components which have marked solubility in the aqueous phase.

Before an aerosol container is discharged into a liquid in a vessel or into an empty vessel to prepare an effervescent product as described by the present invention, it is important to shake the container vigorously to disperse the nomiscible liquefied gas phase throughout the aqueous phase (or to interdisperse all three phases in instances where there may be a lighter than water phase, an aqueous phase and a phase more dense than water, e.g., liquefied gas phase). When emulsifiers capable of emulsifying the liquefied gas phase into the other (usually aqueous) phase are employed, the contents of the container tend to be discharged as a foam rather than as a liquid capable of effervescing. This observation is not surprising since prior art clearly describes the use of emulsifying agents which commonly emulsify the liquefied gas propellant into the remaining compositions of an aerosol container when the objective is to produce a foam such as a whipped topping or a shaving cream. In the preparation of aerosol containers intended for use in producing effervescent liquid compositions, it is generally desirable to avoid incorporating emulsifying agents in sufficient quantity to form a stable emulsion of the liquefied gas phase in the other phase(s) contained in the aerosol container. However, the presence of very small to moderate amounts of emulsifying agents (but insufficient to cause emulsification of the liquefied gas in the other phases) has been found to be very helpful in formulating practical and useful effervescent compositions when the contents of the container are discharged into a liquid in a vessel or into a vessel.

Droplet size of a liquefied gas as affected by orifice size of an aerosol valve or by vigorous impact of the discharged stream into a receptable or a liquid into which the aerosol contents are discharged, is considered to have an effect upon effervescence. Small droplets may tend to vaporize faster and may coalesce into more stable larger droplets. Generally larger orifices are preferred in order to avoid too fine a dispersion of a liquified gas as the contents are discharged from the aerosol container. For example, a series of tests were run with aerosol compositions capable of producing effervescent products. Identical compositions were packed into aerosol containers, the only difference in which was the size of the orifice(s) in the "stem" of the valve assembly. These are the orifices through which liquid contents of the can must pass immediately before the contents reach the valve unit which releases the contents when discharge is desired. Valve assemblies containing stems with orifices as shown below were used:

| No. of Orifices | Diameter of Orifice (inches) |
|---|---|
| 1 | 0.018 |
| 2 | 0.020 |
| 1 | 0.024 |
| 4 | 0.025 |
| 3 | 0.040 |

The products discharged through the above orifices all showed some degree of effervescence but the bubbling action was significantly more vigorous when stems with the larger orifice sizes were used and the stem with three 0.040 inch orifices was definitely better than any of the others.

It is believed that the smaller orifices tend to produce smaller droplets of liquefied gas in the stream of liquid emerging from the aerosol container, while the larger orifices permit larger droplets of liquefied gas to pass through the valve and delivery spout of the aerosol container. As a result of this investigation, it is preferred to use valve assemblies on aerosol containers with larger rather than smaller orifice sizes.

Nucleation centers or micelles in the compositions or matrixes may tend to accelerate vaporization of liquefied gas with attendant foam formation. This effect has been observed when gums such as carrageenans, cellulose derivatives, amylopectins, etc. have been added to a mouthwash composition in an aerosol can. However, an alginate gum (Kelset Algin) has been found to be advantageous for promoting effervescence.

An important consideration which influences and controls the rate and degree of effervescence in products made in the practice of the present invention is the use, in many practical applications, of materials in very small quantities (usually about 0.1% of the aqueous matrix) to promote or control the rate of effervescence. These materials referred to herein as "Additives" vary widely in their chemical nature.

As the examples given in the related applications illustrate, many simple systems combining liquefied gas with aqueous phases in aerosol containers will produce vigorously effervescing compositions when the aerosol container is shaken and some of the contents are discharged either into a vessel or into a vessel containing another liquid, such as water. However, it has been found that when liquefied gas phases are combined with more complex systems, such as flavors, a satisfactory level of effervescence or bubbling of a resulting composition formed by discharging some of the contents of the container into water may frequently be inhibited by some of the ingredients of the aqueous composition.

Usually, this inhibition takes the form of the failure of the liquefied gas component to boil after it, together with the composition, has been discharged into, for example, a vessel containing water. In such a case, the liquefied gas tends to settle to the bottom of the liquid in the vessel into which the composition has been discharged and, even though it is from 20°–100°F. above its boiling point, very little bubbling may occur. The rate of bubbling will be slow (from about 1 bubble per second to perhaps 10 or 20 per second) and usually the size of the bubbles is rather large (number 4 on the Bubble Size Scale reported below). This slow rate of bubbling is considered unsatisfactory for an attractive effervescent composition as compared with the normal bubbling rate which may range from 50 to several hundred bubbles per second.

Additives which have been found particularly effective in counteracting the inhibitory effects of complex systems include but are not limited to the following:

1. Emulsified fatty materials such as:
a. Silicone Antifoam Emulsions which include:
Dow Corning Antifoam A Compound
Dow Corning 200 Fluid
Dow Corning Antifoam C Emulsion
Dow Corning Antifoam FG-10 Emulsions
General Electric Antifoam 10
General Electric Antifoam 71
General Electric Antifoam 72
b. Commercial Whipped Topping Formulations such as:
"Cool-Whip" by General Foods Corporation
c. Coffee Lightener Formulations such as:
"Coffee Mate" by Carnation Company
"Instant Non-Dairy Creamer" by the Great A & P Tea Co.
"Beatreme CW-2 Coffee Whitener" by Beatrice Foods Co.
d. Commercial Mayonnaise such as:
Kraft Mayonnaise by Kraft Foods Co.
Hellmann's Mayonnaise by Best Foods Div., CPC International
2. Sodium Hexametaphosphate
3. an alginate gum (Kelset Algin manufactured by Kelco Company)
4. Sodium Lauryl Sulfonate (Duponol C manufactured by DuPont and Co.)
5. Trisodium salt of ethylenediaminetetraacetic acid; a Chelating Agent (Versene), by Dow Chemical Company Although many of these materials function very effectively at levels of use of about 0.1% of the aqueous phase in an aerosol container, many of them can be used at much higher levels without loss of effectiveness when such higher levels are desirable for their functional effect in a composition. By way of example, sodium hexametaphosphate may be used at levels of 10 to 20% in an aqueous solution in an aerosol container as a water softener in a composition intended to make a bathtub full of water bubble and tingle while imparting a pleasant fragrance to the bath. In such usage, the sodium hexametaphosphate serves the dual function of an Additive to promote vigorous bubbling (for which purpose only 0.1% would be needed) while simultaneously serving as a water softener. Similarly, the alginate gum referred to above may be used in larger quantities for its viscolizing properties while also serving as an Additive to promote vigorous bubbling.

When Additives are used only to promote active bubbling, however, the levels of use will be approximately 0.01–0.2% by weight.

The addition of a small amount (e.g. about 0.1%) of a silicone antifoam composition such as Dow Corning FG-10 to a composition can be used to correct foam formation. If, instead of foaming, the composition formed by discharging a desired amount of aerosol contents into water in a glass does not bubble vigorously, then the various Additives listed above or similar compounds can be added in small quantities (about 0.1%) to the contents of similar containers * Generally, some improvement in the rate of bubbling will be noted with each of the Additives. Combinations of 2, 3 or more Additives are frequently found to be more effective than any single Additive.

* prepared for the purpose of such evaluation.

In the illustrative examples provided below an effervescent scale and a bubble size scale were developed to distinguish differences in effervescence and bubble size. The scales are as follows:

Effervescent Scale

1. Occasional bubbles, just noticeable
2. Slight but steady bubbling
3. Moderate, continuous bubbling
4. Vigorous bubbling (similar to "Alka Seltzer" as tablet dissolves)

Bubble Size Scale

1. Extremely small, below about 0.1 mm; produce cloudy effect which rises slowly to the surface of the product, generally accompanied by a hissing sound
2. Small, between about 0.1 and about 1 mm; similar to a carbonated beverage and accompanied by a sizzling, pinging sound
3. Medium, between about 1 and about 3 mm; similar to bubbles formed as "Alka Seltzer" tablet dissolves and accompanied by crackling, pinging, chirping sound
4. Large, above about 3 mm; similar to air blown into water through a drinking straw, with sounds of bubble forming ("blurp") and bursting ("pop").

Preferably, effervescence and bubble size is each in the range of 2 to 4.

The invention is illustrated and in no sense limited, by the following typical examples.

EXAMPLE 1

An effervescent bath oil is prepared by adding the following components to a conventional aerosol container of a stated 8 ounce capacity:

| | |
|---|---|
| Water | 152 milliliters (ml.) |
| Cologne | 15 ml. |
| (Flueroma Fragrance No. 148 in ethyl alcohol) | |
| Anti-foam agent | 0.02 gram. |

The head-space air above the liquid in the container is essentially swept out by a short burst of gaseous octafluorocyclobutane, and the valve assembly is then mounted and crimped into place in the top of the container. The valve assembly contains a dip tube extending essentially to the bottom of the container so that the contents may be discharged with the container in an upright position. The container is then charged with approximately 48 cubic centimeters of liquid octafluorocyclobutane under pressure using a conventional aerosol filling apparatus. The quantity of octafluorocyclobutane is approximately 32% by weight of the contents of the container. For convenience, the container is then fitted with a discharge spout so designed as to direct a stream generally downwardly when the can is held to an upright or nearly upright position. The pressure of the aerosol container is essentially that corresponding to the vapor pressure of the liquid octafluorocyclobutane at the temperature of the container.

The bath oil in the aerosol container is dispensed therefrom to a tub of hot bath water, as by discharging a stream of the product into the surface of the water. This can be a 4–5 seconds discharge from one end of the tub to the other. Within 10–15 seconds, bubbles begin to burst along the entire surface of the bath water and continue for time intervals of 30 minutes or more. Some liquefied octafluorocyclobutane is discharged along with the aqueous contents of the container and, although some of this fluorinated hydrocarbon will vaporize at the time of discharge, a sufficient quantity will remain in the liquid phase and will tend to be suspended or slowly settle to the bottom of the water in the tub. This liquefied gas, being in the metastable or superheated state, will produce bubbles of gas for extended periods of time. This effervescence or evolution of gas is accompanied by distinct sound effects which at first may consist of a sizzling, particularly if a foamy layer remains on the surface of the water in the tub. The foam will subside usually within a minute or two and when it is gone the sound of the effervescence changes from a "sizzle" to more of a rapid "pinging" or "chirping" sound as individual bubbles of gas are formed in rapid succession. Newly-formed bubbles rising to the surface of the bath water can also be felt by immersed portions of a bather's body. This touch sensation is enhanced as the bather's body moves in the tub, dislodging clusters or bursts of bubbles from the bottom or sides of the tub. This effect of dislodging bursts of bubles from the tub can be repeated a number of times in the same surface areas.

The effervescence created by the bursting bubbles of the liquefied gas serve also to vaporize the delicate fragrances from the perfume oils and other constituents of the cologne used in the composition.

Anti-foam agent C of the Dow Chemical Company, was employed. This is a 30 percent aqueous solution of dimethylpolysiloxane, silica, methyl cellulose and sorbic acid.

EXAMPLE 2

A foot bath preparation is formed by following the procedure given in EXAMPLE 1, above. The following components are added to a conventional, 8 ounce aerosol container:

| | |
|---|---|
| glycerine (U.S.P., 96%) | 50 ml. |
| water | 50 ml. |
| magnesium sulfate (Epsom Salts) | 20 grams. |

Following the procedure of EXAMPLE 1, 7.5 ml. of dichlorodifluoromethane (Freon 12) and 22.5 ml. of trichloromonofluoromethane (Freon 11), are then charged to the container.

A portion of the contents of the container is discharged into foot bath containing hot water, in a 2–3 seconds burst. results achieved correspond to those described in connection with EXAMPLE 1.

The Examples of TABLE 1 illustrate additional cosmetic compositions and the effect of Additives. The Additives are indicated by an asterisk(*).

TABLE 1

| FORMULA NO. | INGREDIENTS | CAN AT REFRIGERATION TEMP. | CAN AT ROOM TEMP. |
|---|---|---|---|
| 28-11-A | CHAMPAGNE BATH: | | |
| | 150 ml. water | About 20 gms. of material | About 20 gms. of material |
| | 5.0 gms. Sodium Hexametaphosphate | squirted into water at 120°F. | squirted into water at 120°F. |
| | 10.0 ml. Cologne 25-139-C$^a$ | contained in 4 qt. size bowl. | contained in 4 qt. size bowl. |
| | 0.2 gms. Kelset Algin* | Effervescent Scale: 4 | Effervescent Scale: Cloudy |
| | 5 ml. 4% soln. A&P coffee lightener* | Bubble Size Scale: 2–3 | Initially, then 2–3 |
| | 8 drops 20% soln. Dow Antifoam "C" | | Bubble Size Scale: 3 |
| | 60 ml. Freon 114 | | |
| | a = Cologne 25-139-C: Made as 1 ml. Fleuroma Fragrance No. 148, dissolved in 50 ml. pure ethyl alcohol. | | |
| 28-110-1 | CHAMPAGNE BATH: | | |
| | 150 ml. water | About 20 gms. of material | About 20 gms. of material |
| | 5.0 gms. Sodium Hexametaphosphate | squirted into water at 120°F. | squirted into water at 120°F. |
| | 10 ml. Cologne 25-139-C | contained in 4 qt. size bowl. | contained in 4 qt. size bowl |
| | 60 ml. Freon 114 | Effervescent Scale: Initially 3–4, then 2–3 | Effervescent Scale: 1–2 |
| | | Bubble Size Scale: Initially combination of 2 and 3, then of 3 and 4. | Bubble Size Scale: 1–2 also cloudy initially |
| 28-53-4 | FOOT BATH: | | |
| | 150 ml. water | same as 28-11-A | same as 28-11-A |
| | 3 drops Oleo Resin Capsicum | | |
| | 30 gms. Magnesium Sulfate | | |
| | 0.2 gm. Kelset Algin* | | |
| | 5 ml. 4% soln. A&P coffee lightener* | | |
| | 10 drops 20% soln. Dow Antifoam "C" | | |
| | 60 ml. Freon 114 | | |
| 28-110-2 | FOOT BATH: | | |
| | 150 ml. water | used same as above | used same as above |
| | 30 gms. Magnesium Sulfate | Effervescent Scale: Initially 3, then 2 | Effervescent Scale: 1–2 |
| | 60 ml. Freon 114 | | Bubble Size Scale: 1–2 |

TABLE 1-continued

| FORMULA NO. | INGREDIENTS | CAN AT REFRIGERATION TEMP. | CAN AT ROOM TEMP. |
|---|---|---|---|
| | | Bubble Size Scale: Initially 4, then 3. | also cloudy initially |

Proprietary materials used in formulations shown above include the following:

Sucaryl Blend 110 CS comprises 1 part of saccharin and 10 parts of cyclamate; marketed by Abbott Laboratories;

Kelset Algin is an algin product; it is a light ivory, fibrous powder, neutral pH, mesh size of approximately 80; marketed by Kelco Company;

Dow Corning Antifoam C is a water-dilutable silicone emulsion containing 30% active defoamer; specific gravity at 77°F. of 1.003; pH 3.9; marketed by Dow Corning;

Dow Corning Antifoam FG-10 Emulsion is a water-dilutable defoamer containing 10 percent of Dow Corning Antifoam A compound, food grade; specific gravity at 77°F. of 1.003; pH 3–5; marketed by Dow Corning;

Beatreme CW-2 Coffee Whitener (non-dairy type) contains vegetable fat, corn syrup solids, sodium caseinate, mono and diglycerides, dipotassium phosphate, sodium silico aluminate, artificial flavor and color; fat content is 51.0% (± 1.5%); moisture, 2.5% maximum; protein, 4.5% maximum; marketed by Beatrice Foods Company.

Numerous modifications and variations of the invention may be made without departing from the spirit and scope thereof. Accordingly, it is to be understood that the invention is not to be limited, but is to be construed in the light of the language of the appended claims.

What is claimed is:

1. An effervescing cosmetic composition confined under pressure in an aerosol dispensing container, said cosmetic composition consisting essentially of (a) a liquefied gas having a boiling point of from about −50°F. to about 80°F. and an aqueous or alcoholic phase (b) containing a liquid cosmetic and being substantially free of an agent capable of emulsifying the liquefied gas (a) in said phase (b), said phase (b) being substantially non-soluble with (a) and being dispersible with (a) with agitation thereof, liquefied gas (a) having a density greater than (b) and the quantity of (a) being at least about 5 percent by weight in excess of the quantity required to propel (b) from said container, said cosmetic composition being characterized by effervescence when said aerosol container is agitated whereupon (a) is dispersed in (b), and, while (a) and (b) are interdispersed, discharging contents of the container as a liquid stream into a vessel, some of the dispersed liquefied gas (a) remaining dispersed and entrained as a liquid in said liquid stream after the contents leave the container.

2. The composition of claim 1 containing about 32 percent by weight of octafluorocyclobutane.

3. A composition of claim 1, wherein the container is at a temperature below about 50°F.

4. A composition of claim 1, wherein the vessel contains a liquid.

5. A composition of claim 1, wherein the liquefied gas is octafluorocyclobutane or monochloropentafluoroethane.

6. A composition of claim 1, wherein the cosmetic is a bath oil.

7. A composition of claim 1, wherein the cosmetic is a foot bath preparation.

8. A composition of claim 1, wherein the cosmetic is a facial preparation.

9. A composition of claim 1 containing a mixture of said liquefied gases.

* * * * *